United States Patent
Katuwal et al.

(10) Patent No.: US 11,657,920 B2
(45) Date of Patent: May 23, 2023

(54) DYNAMIC AND LOCALLY-FAITHFUL EXPLANATION OF MACHINE LEARNING MODELS FOR PRECISION MEDICINE

(71) Applicant: KONINKLIJKE PHILIPS N.V., Eindhoven (NL)

(72) Inventors: Gajendra Jung Katuwal, Cambridge, MA (US); Bryan Conroy, Garden City, NY (US); Jonathan Rubin, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 410 days.

(21) Appl. No.: 16/880,250

(22) Filed: May 21, 2020

(65) Prior Publication Data
US 2021/0012897 A1    Jan. 14, 2021

Related U.S. Application Data

(60) Provisional application No. 62/871,501, filed on Jul. 8, 2019.

(51) Int. Cl.
| | |
|---|---|
| G16H 50/20 | (2018.01) |
| G06F 17/16 | (2006.01) |
| G06N 5/00 | (2023.01) |
| G06N 20/00 | (2019.01) |

(52) U.S. Cl.
CPC .............. *G16H 50/20* (2018.01); *G06F 17/16* (2013.01); *G06N 5/003* (2013.01); *G06N 20/00* (2019.01)

(58) Field of Classification Search
CPC ........ G16H 50/20; G06N 20/00; G06N 5/003; G06F 17/16
See application file for complete search history.

(56) References Cited

U.S. PATENT DOCUMENTS

| | | | |
|---|---|---|---|
| 7,653,556 B2 | 1/2010 | Marek et al. | |
| 8,818,782 B2 | 8/2014 | Chittajallu et al. | |
| 9,913,616 B2 | 3/2018 | Fonte et al. | |
| 2011/0257988 A1* | 10/2011 | Denekamp | G16H 50/30 |
| | | | 706/54 |
| 2017/0140109 A1* | 5/2017 | Kheifetz | G16H 50/20 |
| 2019/0221311 A1* | 7/2019 | Takeuchi | G16H 50/20 |

(Continued)

OTHER PUBLICATIONS

Erion G, Chen H, Lundberg SM, Lee Si. Anesthesiologist-level forecasting of hypoxemia with only SpO2 data using deep learning. arXiv preprint arXiv:1712.00563. Dec. 2, 2017. (Year: 2017).*

(Continued)

*Primary Examiner* — Chuen-Meei Gan
(74) *Attorney, Agent, or Firm* — Sherry Austin

(57) ABSTRACT

A method of explaining a machine learning model, including: receiving a plurality of disease states for a patient over time from a database, wherein the disease states have a plurality of features; generating a plurality of locally faithful explanation models for the patient for each disease state based upon the machine learning model; calculating an explanation with respect to one feature of the plurality of features over time using the locally faithful explanation models; and calculating the importance of the one feature of the plurality of features over time based upon the plurality of locally faithful explanation models.

20 Claims, 5 Drawing Sheets

(56) References Cited

U.S. PATENT DOCUMENTS

2019/0304603 A1* 10/2019 Takata .................. G06N 20/00

OTHER PUBLICATIONS

Lundberg SM, Erion G, Chen H, DeGrave A, Prutkin JM, Nair B, Katz R, Himmelfarb J, Bansal N, Lee Si. Explainable AI for trees: From local explanations to global understanding. arXiv preprint arXiv:1905.04610. May 11, 2019. (Year: 2019).*

Lundberg SM, Lee Si. A unified approach to interpreting model predictions. Advances in neural information processing systems. 2017; (Year: 2017).*

Ribeiro, M.T. et al., "Why should I trust you?: Explaining the Predictions of any Classifier," 2016.

Katuwal, G.J. et al., "Machine Learning Model Interpretability for Precision Medicine," Computer Science. Machine Learning, Proceedings of the 2016 Conference of the North American Chapter of the Association for Computational Linguistics, Oct. 2016.

\* cited by examiner

DYNAMIC AND LOCALLY-FAITHFUL EXPLANATION OF MACHINE LEARNING MODELS FOR PRECISION MEDICINE

TECHNICAL FIELD

Various exemplary embodiments disclosed herein relate generally to dynamic and locally-faithful explanation of machine learning models for precision medicine.

BACKGROUND

Generally, there is a trade-off between the predictive power and interpretability of machine learning models; the more accurate machine learning models tend to be more complex and hence are difficult to interpret. In this trade-off, model interpretability is as important as the accuracy of the model. The importance of model explanations is particularly important in healthcare because it involves the lives of people. The model explanation that is locally faithful to a particular data point (i.e., a medical case in this case) is inherently suitable for precision medicine. The insightful model explanations tailored to the unique disease state of a patient can be very valuable for their effective diagnosis/treatment.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a method of explaining a machine learning model, including: receiving a plurality of disease states for a patient over time from a database, wherein the disease states have a plurality of features; generating a plurality of locally faithful explanation models for the patient for each disease state based upon the machine learning model; calculating an explanation with respect to one feature of the plurality of features over time using the locally faithful explanation models; and calculating the importance of the one feature of the plurality of features over time based upon the plurality of locally faithful explanation models.

Various embodiments are described, further including presenting on a graphical user interface a plot of the explanation and importance of the one feature of the plurality of features over time.

Various embodiments are described, wherein the locally faithful explanation models are a linear model $y=\beta x$, where y is the value of the machine leaning model, x is a feature vector, and $\beta$ is a vector of linear coefficients that are explanations for each feature in the vector x.

Various embodiments are described, wherein the explanation of a feature $x_k$ at time t is:

$$\beta_k^t = \frac{\Delta y}{\Delta x_k}\bigg|_t.$$

Various embodiments are described, wherein the importance of feature $x_k$ at time t is:

$$I_k^t = \frac{\beta_k}{\Sigma \beta}\bigg|_t * 100.$$

Various embodiments are described, wherein generating a plurality of locally faithful explanation models for the patient for each disease state includes optimizing $$\xi(x) = \min_{g \in G} L\left(f, g, \prod_x\right) + \Omega(g),$$

where $\xi(x)$ is the optimal model explanation that minimizes the sum of loss L and complexity measure, g is a locally faithful explanation model, f is the machine leaning model being explained, $L(f, g, \Pi_x)$ is the measure of how unfaithful g is in approximating f in the locality defined by $\Pi_x$, and $\Omega(g)$ is the complexity of g based upon the number of parameters of g.

Various embodiments are described, wherein $\Omega(g)$ is the number of non-zero coefficients when g is a linear model.

Various embodiments are described, wherein $\Omega(g)$ is the depth of a decision three when g is a decision tree.

Further various embodiments relate to a method of explaining machine learning models, including: receiving a plurality of disease states for a patient over time from a database, wherein the disease states have a plurality of features; generating a plurality of locally faithful explanation models for the patient for each disease state based upon the machine learning model; calculating an explanation with respect to one feature of the plurality of features over time using the locally faithful explanation models; and calculating the average explanation of the one feature of the plurality of features over a specific time period based upon the plurality of locally faithful explanation models.

Further various embodiments relate to a method of explaining machine learning models, including: receiving a plurality of disease states for a patient over time from a database, wherein the disease states have a plurality of features; generating a plurality of locally faithful explanation models for the patient for each disease state based upon the machine learning model; calculating an explanation with respect to one feature of the plurality of features over time using the locally faithful explanation models; and calculating the average explanation of the one feature of the plurality of features over a specific time period based upon the plurality of locally faithful explanation models.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION

Figure 1:
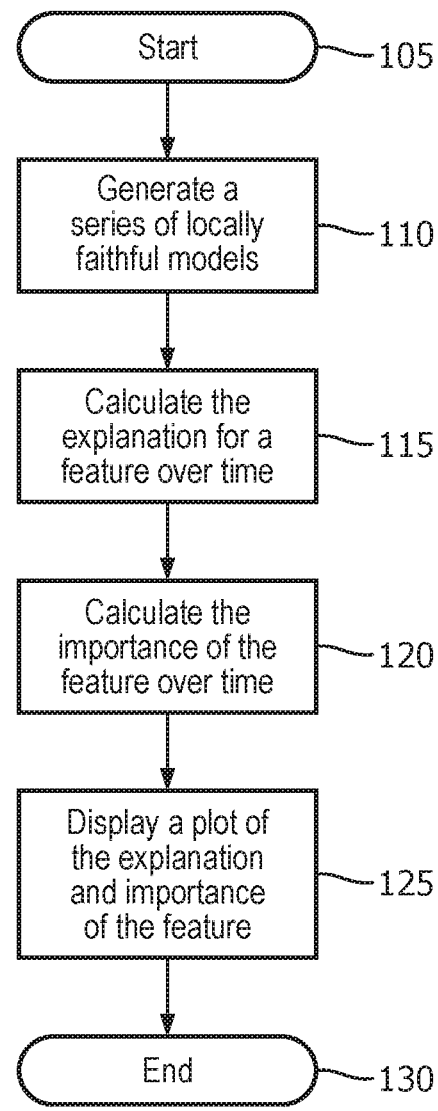
FIG. 1 illustrates a method used by the explanation system to provide a longitudinal view of model explanation.

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

A recent machine learning technique called locally-interpretable model-agnostic explanations (LIME) is particularly suitable for application in precision medicine. LIME has already been utilized to generate patient specific model explanations for mortality prediction of ICU patients. Embodiments will be described herein applying lime to patient data in order to gain a longitudinal view of model explanation, to determine an average model explanation within a certain time period, and for future prediction of explanation with the need for fitting the full model.

A medical case associated with a patient is not in a static state, but rather is in a dynamic state where the state parameters are continuously changing with time. A longitudinal view of a patient as shown by a series of disease states or a patient history provides much more information than a single disease state. However, the current existing solutions for machine learning model explanations in healthcare treat a medical case as a static case and focus on generating model explanations for a patient at only one point. The insightful model explanations tailored to the unique disease state of a patient at a single time point is a valuable in its own right. However, by neglecting the dynamic nature of patient medical state, the significant information along the time dimension may be lost which may be valuable for the optimum management of the patient.

An embodiment of a framework to generate dynamic model explanations for a patient using simpler models that mimic the complex model locally around the patient state are described herein, using for example the LIME approach. A benefit of this approach is that the case where the patient disease state is continuously changing may be handled.

The framework may be used to derive: 1) a longitudinal view of model explanation for a data point (or patient of interest); 2) average model explanation within a certain time period; or 3) future prediction of explanation without the need of fitting the full model. The framework models a medical case as a time varying dynamic state and utilize explanation techniques such as for example LIME to generate dynamic model explanations.

Now a more detailed description of the explanation system will be given. Let $x \in R_d$ be an instance or the patient of interest being explained. Let the model being explained be denoted f: $R_d \rightarrow R$. In a classification model, f(x) is the probability (or a binary indicator) that x belongs to a certain class. In a regression model, f(x) is the output value modeled.

Next, an explanation or a model g is to be found that is human-interpretable, simple, and locally faithful to f. Interpretability is introduced in model explanation in two steps. First, the explanation model is chosen such that $g \in G$ where G is a class of potentially human-interpretable models. The most agreed upon type of such models are linear models, decision trees, falling rule lists, etc. Second, the data instance itself is made interpretable by g acts over absence/presence of the interpretable components.

In order to force g to be simple enough, its complexity as measured by $\Omega(g)$ may be minimized. $\Omega(g)$ is proportional to the number of parameters of g. For example, for a decision tree, $\Omega(g)$ may be its depth and for a sparse linear model, $\Omega(g)$ may be the number of non-zero coefficients.

To ensure that g is locally faithful to f in the vicinity of the data point of interest x (e.g., a medical case), a set of instances are sampled around x, and the interpretable form of them are used to build g. The locality around x is defined by a locality function $\Pi_x$ where $\Pi_x(z)$ is a proximity measure between a sample instance z to x.

Finally, the model explanation g is found as:

$$\xi(x) = \min_{g \in G} L\left(f, g, \prod_x\right) + \Omega(g),$$

where L(f, g, $\Pi_x$) is the measure of how unfaithful g is in approximating f in the locality defined by $\Pi_x$ and $\xi(x)$ is the optimal model explanation that minimizes the sum of loss L and complexity measure. This optimization problem may be solved using various methods.

The following explanation method is used by the explanation system. The model explanation g will be used to calculate the feature explanation or role (i.e., how a feature affects the dependent variable) and feature importance (i.e., how important is a feature to predict the dependent variable) in the vicinity of the data point of interest x. Instead of deriving a single model explanation by calculating g at only one time point like other techniques, the explanation system derives a series of model explanations by calculating a different model explanation g at each time point. A patient P may be modeled as a series of disease states, $$P=[x^t]$$

where $x^t$ is a disease state at time point t.

Next, the series of locally faithful models at each time point are calculated for the patient P as $$G=[g^t]$$

where $g^t$ is a simple interpretable model at time point t which is locally faithful for the patient P.

In this embodiment, a sparse linear model will be used as an example, but the explanation method may utilize any other human-interpretable models. If g is a sparse linear model, $$y=\beta x$$

where $\beta$ are the coefficients of g, then, for a data point x (i.e., a state of the patient of interest), the explanation (role) of feature $x_k$ at time t is:

$$\beta_k^t = \frac{\Delta y}{\Delta x_k}\bigg|_t.$$

The importance of feature $x_k$ at time t is:

$$I_k^t = \frac{\beta_k}{\Sigma \beta}\bigg|_t * 100.$$

These calculations may be used in the following situations to help explain a model of the patient.

FIG. 1 illustrates a method used by the explanation system to provide a longitudinal view of model explanation. First, the method starts 105, and the explanation system generates a series of locally faithful models 110 as described above. Next, the explanation system calculates the explanation for a feature over time 115 as described above. Then the explanation system calculates the importance of the feature over time 120. Finally, the explanation system displays a plot of the explanation and importance of the feature 125, and then the method ends 130. This plot may be viewed by a healthcare provider to gain insight regarding the model of the patient and also which features are important in describing the state of the patient. An example of such plots will now be provided and described.

Figure 2:
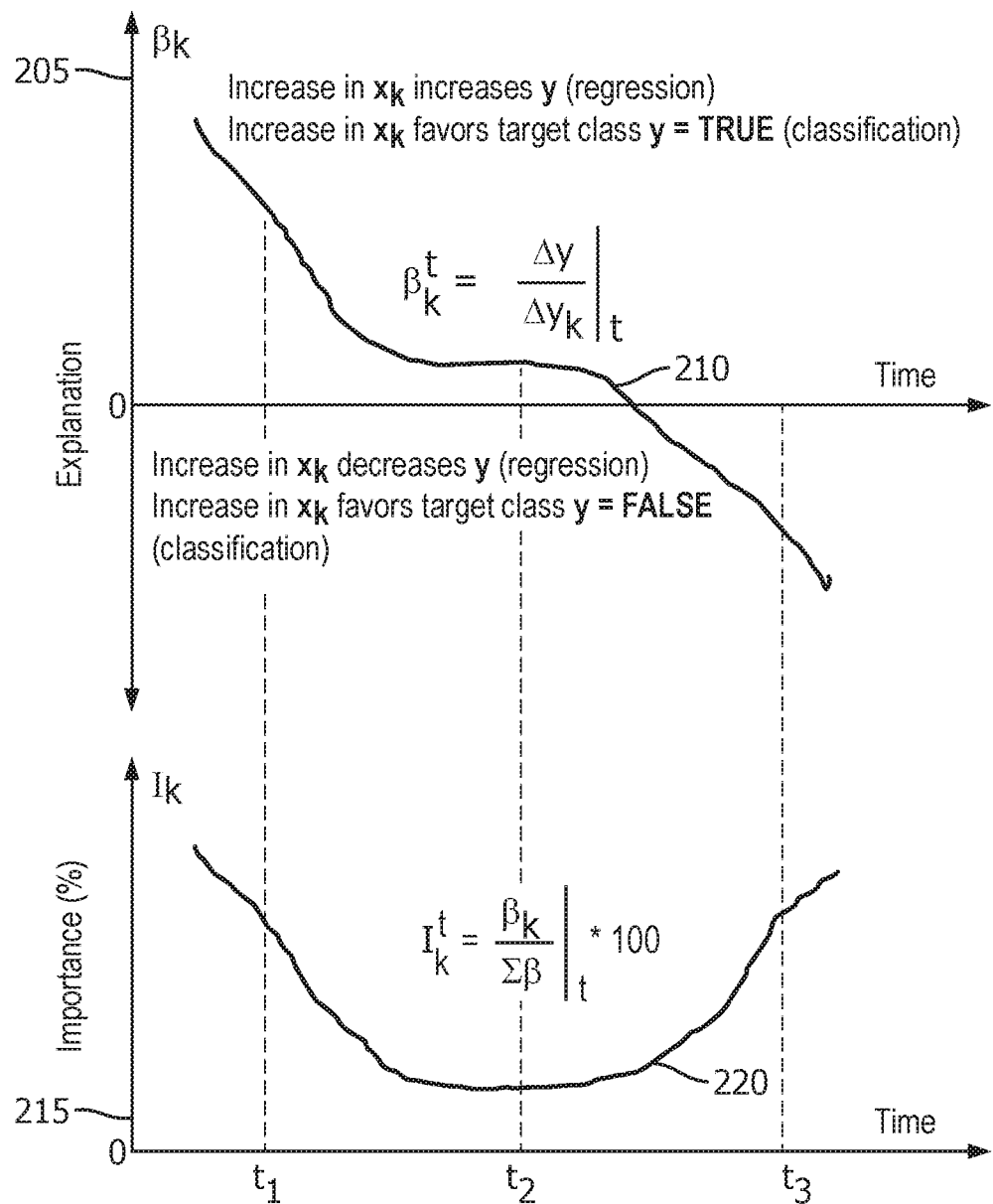
FIG. 2 illustrates two plots: a plot of explanation versus time, and a plot of importance versus time.

FIG. 2 illustrates two plots: a plot of explanation versus time, and a plot of importance versus time. Given the model explanation and feature importance from time points $t_1$ to $t_3$, how model decision process changes with time for the patient of interest may be visualized.

The top plot is a plot of model explanation $\beta_k^t$ versus time for a feature $x_k$ that illustrates how the feature role or explanation for feature $x_k$ affects the dependent variable y. From time $t_1$ to $t_2$, an increase in $x_k$ increases y for a regression model or favors class y=TRUE for a classification model. For this example, a classification model will be explained. Here, the feature $x_k$ strongly favors class y=TRUE initially at time point $t_1$. The favor decreases with time and then value for y flips and the feature $x_k$ starts favoring class y=FALSE around time point $t_3$.

The bottom plot is a plot of the importance $I_k^t$ of feature $x_k$ that illustrates the contribution of feature $x_k$ to predict the dependent variable y. The feature importance which is initially high around time point $t_1$ decreases around time point $t_2$ and then again increases around time point $t_3$. This tracks with the model explanation where at $t_1$ and $t_3$ the explanation has a clearer and distinct value, but at time $t_2$ the value is low showing that at this time the feature $x_k$ does not contribute much to the prediction of the variable y.

With this information and such plots, several insightful questions can be answered. For example:

How do the important features change with time? That is plots for the various features may be used to identify which features are important in affecting the output. Then these features can be observed over time to see how they change.

How does the role of a feature change with time? Such as, how does an increase in patient temperature affect the mortality rate of a patient in ICU?

How does the importance of a feature change with time? For example, does a specific vital sign become more or less important to the patient over time?

How does the correlation of feature importance and the dependent variable change with time? For example, as the value of the importance changes does it track the value of the dependent value in the same way?

How does the model explanation differ between two time points? See the examples in FIG. 2.

What higher order information of model explanation can be identified? For example, how fast the importance of a feature changes with time or when does the flipping of the role of a feature occur?

Considering and evaluating such questions can provide a healthcare provider greater insight into how a patient's health progresses, what treatments or measured parameters affect certain outcomes, etc.

Figure 3:
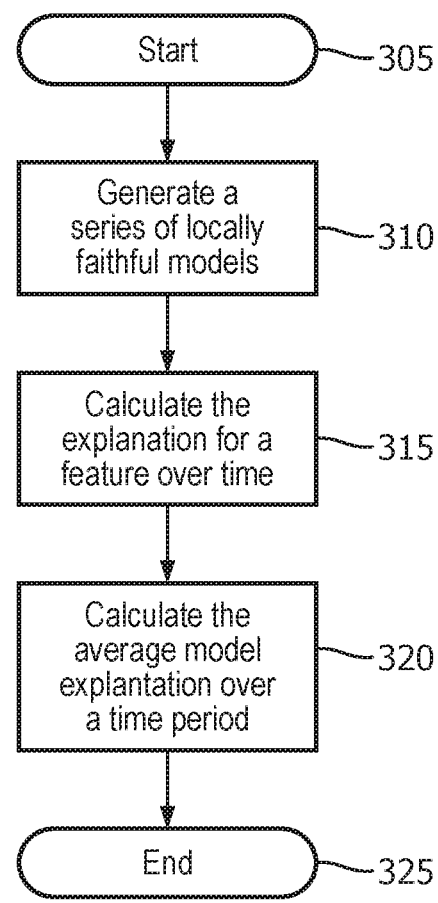
FIG. 3 illustrates a method used by the explanation system to provide average model explanation within a certain time period.

FIG. 3 illustrates a method used by the explanation system to provide average model explanation within a certain time period. First, the method starts 305, and the explanation system generates a series of locally faithful models 310 as described above. Next, the explanation system calculates the explanation for a feature over time 315 as described above. Then the explanation system calculates the average model explanation over a certain time period 320. Finally, the method ends 325. Given the model explanations between two time points $t_1$ and $t_2$, the average of the model explanation within the time period can be computed as:

$$\beta^{t_1,t_2} = \frac{1}{t_2 - t_1} \frac{1}{\sum \theta} \sum_{t=t_1}^{t_2} \theta^t \beta^t$$

where $\beta^t$ and $\theta^t$ are the model explanation and the model confidence at time t. Model confidence may be estimated in many ways and should be related to the predictive performance of the model f. In classification settings, for example, the model confidence at time t can be computed from the distance of the model's output at time t from the classification decision boundary With this information, various insightful questions may be answered. For example, for the patient of interest, how do feature roles and feature importance differ during weekday and weekends, days and nights, etc.?

Figure 4:
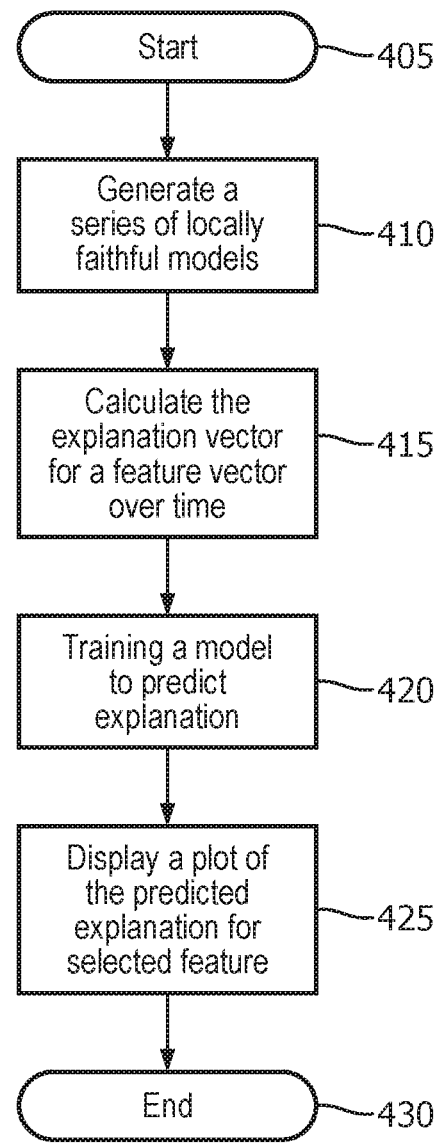
FIG. 4 illustrates a method to produce a model to predict explanation.

FIG. 4 illustrates a method to produce a model to predict explanation. First, the method starts 405 and the explanation system generates a series of locally faithful models 410 as described above. Next, the explanation system calculates an explanation vector for a feature vector over time 415 as described above. Then the explanation system trains a model to predict the explanation 420. This prediction model be calculated as:

$$\beta^{t+1} = \varphi([\beta^{t-t_0}, \ldots, \beta^t])$$

where $\varphi$ is a model trained in the series of multi-dimensional model explanation vectors $\beta^t$. The model $\varphi$ may be any forecasting model that predicts future values from past explanation vectors (e.g., auto-regressive models). This explanation model may be used to predict model explanation without building the original model f and its approximation g. Finally, the explanation system displays a plot of the explanation and predicted explanation values for the feature 425, and then the method ends 430. This plot may be viewed by a healthcare provider to see predicted values of the explanation for a selected feature. This allows for the future prediction of explanation without the need of fitting the full model.

Figure 5:
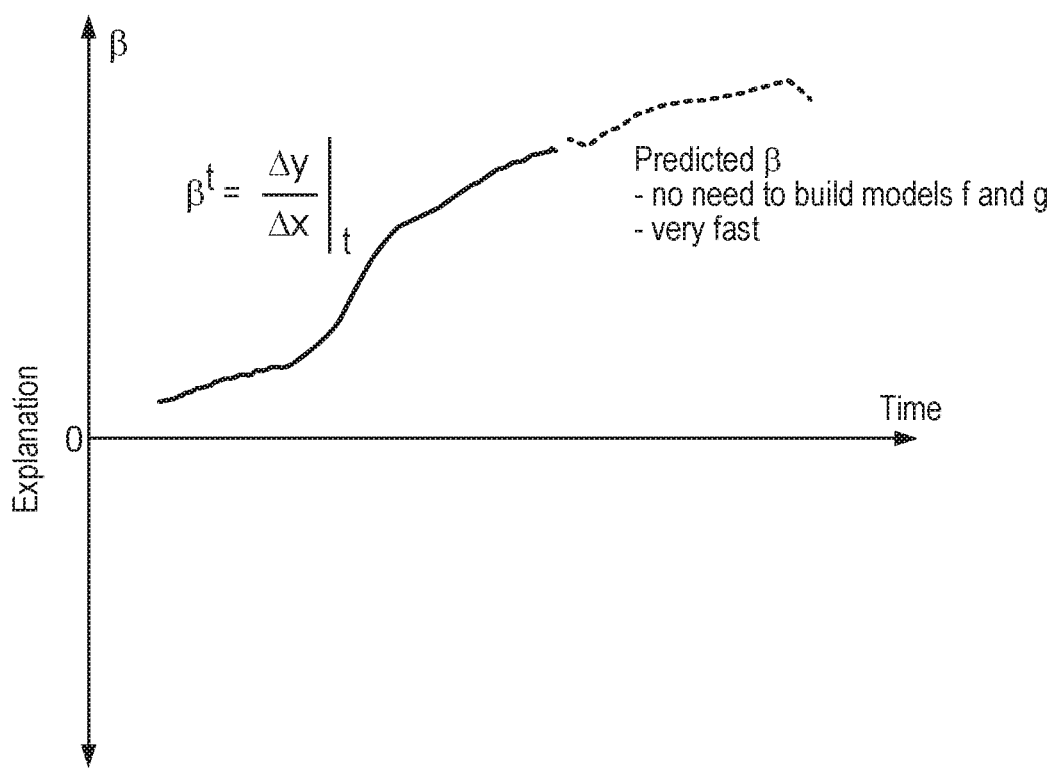
FIG. 5 illustrates a plot of the explanation for a selected feature, where the plot includes predicted explanation values.

FIG. 5 illustrates a plot of the explanation for a selected feature, where the plot includes predicted explanation values. This is done without the fitting of the full model. This explanation prediction model may be useful when the original model f training time is high and/or there is an immediate need of model explanations for a patient; for example, in an emergency situation. It may also be useful to extrapolate the model explanations when there is no future data available for the patient. In addition, it may be useful to approximate the model explanation when the original data is not available for the patient of interest.

There are various applications of the explanation system described herein. For example, precision medicine, interpretable machine learning in healthcare, therapy decision support, etc.

The embodiments of an explanation system described herein solve the technological problem of explaining a machine learning model used in treating and/or evaluating a patient. Training an explanation model for a model to be explained can be time consuming and complex. In order to overcome these issues, a plurality of localized models are developed at various points in time. These localized models may then be used to calculate model explanation and importance metrics for various features. Further, an average model explanation over a time period may be calculated to provide various insights. Finally, future values of the model explanation may be generated using the localized models. This method leads to results and insights requiring less processing than if the full models were trained and then calculated.

The embodiments described herein may be implemented as software running on a processor with an associated memory and storage. The processor may be any hardware device capable of executing instructions stored in memory or storage or otherwise processing data. As such, the processor may include a microprocessor, field programmable gate array (FPGA), application-specific integrated circuit (ASIC), graphics processing units (GPU), specialized neural network processors, cloud computing systems, or other similar devices.

The memory may include various memories such as, for example L1, L2, or L3 cache or system memory. As such, the memory may include static random-access memory (SRAM), dynamic RAM (DRAM), flash memory, read only memory (ROM), or other similar memory devices.

The storage may include one or more machine-readable storage media such as read-only memory (ROM), random-access memory (RAM), magnetic disk storage media, optical storage media, flash-memory devices, or similar storage media. In various embodiments, the storage may store instructions for execution by the processor or data upon with the processor may operate. This software may implement the various embodiments described above.

Further such embodiments may be implemented on multiprocessor computer systems, distributed computer systems, and cloud computing systems. For example, the embodiments may be implemented as software on a server, a specific computer, on a cloud computing, or other computing platform.

Any combination of specific software running on a processor to implement the embodiments of the invention, constitute a specific dedicated machine.

As used herein, the term "non-transitory machine-readable storage medium" will be understood to exclude a transitory propagation signal but to include all forms of volatile and non-volatile memory.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A method of explaining a machine learning model, comprising:
   receiving, by a processor, a plurality of disease states for a patient over time from a database, wherein the disease states have a plurality of features;
   generating, by the processor, a plurality of locally faithful explanation models for the patient for each disease state;
   calculating, by the processor, an explanation with respect to one selected feature of the plurality of features over time using the locally faithful explanation models, wherein the locally faithful explanation models are a linear model y=βx, where y is the value of the machine learning model, x is a feature vector, and β is a vector of linear coefficients that are explanations for each feature in the vector x;
   calculating, by the processor, the importance of the one selected feature of the plurality of features over time based upon the plurality of locally faithful explanation models; and
   providing, by the processor, the importance of the one selected feature of the plurality of features over time for evaluating the plurality of disease states of the patient.

2. The method of claim 1, further comprising presenting on a graphical user interface a plot of the explanation and importance of the one selected feature of the plurality of features over time.

3. The method of claim 1, wherein the explanation of a feature $x_k$ at time t is:

$$\beta_k^t = \left.\frac{\Delta y}{\Delta x_k}\right|_t.$$

4. The method of claim 3, wherein the importance of feature $x_k$ at time t is:

$$I_k^t = \left.\frac{\beta_k}{\Sigma \beta}\right|_t * 100.$$

5. The method of claim 1, wherein generating a plurality of locally faithful explanation models for the patient for each disease state includes optimizing $$\xi(x) = \min_{g \in G} L\left(f, g, \prod_x\right) + \Omega(g),$$

where ξ(x) is the optimal model explanation that minimizes the sum of loss L and complexity measure, g is a locally faithful explanation model, f is the machine leaning model being explained, L(f, g, Πx) is the measure of how unfaithful g is in approximating f in the locality defined by Πx, and Ω(g) is the complexity of g based upon the number of parameters of g.

6. The method of claim 5, wherein Ω(g) is the number of non-zero coefficients when g is a linear model.

7. The method of claim 5, wherein Ω(g) is the depth of a decision three when g is a decision tree.

8. A method of explaining machine learning models, comprising:
- receiving, by a processor, a plurality of disease states for a patient over time from a database, wherein the disease states have a plurality of features;
- generating, by the processor, a plurality of locally faithful explanation models for the patient for each disease state;
- calculating, by the processor, an explanation with respect to one selected feature of the plurality of features over time using the locally faithful explanation models, wherein the locally faithful explanation models are a linear model y=βx, where y is the value of the machine learning model, x is a feature vector, and β is a vector of linear coefficients that are explanations for each feature in the vector x;
- calculating, by the processor, the average explanation of the one selected feature of the plurality of features over a specific time period based upon the plurality of locally faithful explanation models; and
- providing, by the processor, the average explanation of the one selected feature of the plurality of features over the specific time period for evaluating the plurality of disease states of the patient.

9. The method of claim 8, further comprising presenting on a graphical user interface a plot of the average explanation of the one selected feature of the plurality of features over the specific time period.

10. The method of claim 8, wherein the explanation of a feature $x_k$ at time t is:

$$\beta_k^t = \frac{\Delta y}{\Delta x_k}\bigg|_t.$$

11. The method of claim 10, wherein the average importance of feature $x_k$ over time $t_1$, to $t_2$, is $$\beta^{t_1,t_2} = \frac{1}{t_2 - t_1} \frac{1}{\Sigma \theta} \sum_{t=t_1}^{t_2} \theta^t \beta^t,$$

where $\theta^t$ is the model confidence.

12. The method of claim 8, wherein generating a plurality of locally faithful explanation models for the patient for each disease state includes optimizing $$\xi(x) = \min_{g \in G} L\left(f, g, \prod_x\right) + \Omega(g),$$

where $\xi(x)$ is the optimal model explanation that minimizes the sum of loss L and complexity measure, g is a locally faithful explanation model, f is the machine leaning model being explained, L(f, g, Πx) is the measure of how unfaithful g is in approximating f in the locality defined by Πx, and Ω(g) is the complexity of g based upon the number of parameters of g.

13. The method of claim 12, wherein Ω(g) is the number of non-zero coefficients when g is a linear model.

14. The method of claim 12, wherein Ω(g) is the depth of a decision three when g is a decision tree.

15. A method of producing a model to predict the explanation of a machine learning models, comprising:
- receiving, by a processor, a plurality of disease states for a patient over time from a database, wherein the disease states have a plurality of features;
- generating, by the processor, a plurality of locally faithful explanation models for the patient for each disease state;
- calculating, by the processor, an explanation vector based on the plurality of features over time using the locally faithful explanation models, wherein the locally faithful explanation models are a linear model y=βx, where y is the value of the machine learning model, x is a feature vector, and β is a vector of linear coefficients that are explanations for each feature in the vector x;
- training, by the processor, a prediction model to predict the explanation of the machine learning model based upon the explanation vector; and
- providing, by the processor, the explanation of the machine learning model for evaluating the plurality of disease states of the patient.

16. The method of claim 15, further comprising presenting on a graphical user interface a plot of a prediction of the explanation of the machine learning model over time.

17. The method of claim 15, wherein the explanation of a feature $x_k$ at time t is $$\beta_k^t = \frac{\Delta y}{\Delta x_k}\bigg|_t.$$

18. The method of claim 15, wherein generating a plurality of locally faithful explanation models for the patient for each disease state includes optimizing $$\xi(x) = \min_{g \in G} L\left(f, g, \prod_x\right) + \Omega(g),$$

where $\xi(x)$ is the optimal model explanation that minimizes the sum of loss L and complexity measure, g is a locally faithful explanation model, f is the machine leaning model being explained, L(f, g, Πx) is the measure of how unfaithful g is in approximating f in the locality defined by fix, and Ω(g) is the complexity of g based upon the number of parameters of g.

19. The method of claim 18, wherein Ω(g) is the number of non-zero coefficients when g is a linear model.

20. The method of claim 18, wherein, Ω(g) is the depth of a decision three when g is a decision tree.

* * * * *